United States Patent
Kimes et al.

[11] Patent Number: 6,108,886
[45] Date of Patent: Aug. 29, 2000

[54] METHOD AND APPARATUS FOR UNIFORMLY CRIMPING A STENT ONTO A CATHETER

[76] Inventors: Richard M. Kimes, 1315 Savannah La., Carlsbad, Calif. 92009; Michael S. Mirizzi, 2022 Foxhall Loop, San Jose, Calif. 95125

[21] Appl. No.: 09/340,967

[22] Filed: Jun. 28, 1999

Related U.S. Application Data

[63] Continuation of application No. 09/072,925, May 5, 1998.
[51] Int. Cl.$^7$ .................................................. A61M 29/00
[52] U.S. Cl. ............................... 29/280; 606/198; 623/1; 29/516; 29/282; 29/203.5
[58] Field of Search ..................... 29/282, 283.5, 29/516, 517, 407.08, 280, 715, 423, 234, 235, 283, 269, 270; 606/108, 198, 1

[56] References Cited

U.S. PATENT DOCUMENTS

| | | |
|---|---|---|
| 696,289 | 3/1902 | Williams . |
| 3,619,885 | 11/1971 | Dischler . |

(List continued on next page.)

FOREIGN PATENT DOCUMENTS

| | | |
|---|---|---|
| 0 826 346 | 3/1998 | European Pat. Off. . |
| 11-192309 | of 1999 | Japan . |
| 159065 | 2/1921 | United Kingdom . |
| WO 98/14120 | 4/1998 | WIPO . |
| WO 98/19633 | 5/1998 | WIPO . |

OTHER PUBLICATIONS

U.S Patent Application Serial No. 08/795,335 filed Feb. 4, 1997.
U.S. Patent Application Serial No. 08/837,771 filed Apr. 22, 1997.
U.S. Patent Application Serial No. 08/089,936 filed Jul. 15, 1997.
U.S. Patent Application Serial No. 08/962,632 filed Nov. 3, 1997.

*The eXTraordinary Stent*, C.R. Bard Brochure (Undated).

*Primary Examiner*—David P. Bryant
*Assistant Examiner*—Steven A Blount
*Attorney, Agent, or Firm*—Fulwider Patton Lee & Utecht, LLP

[57] ABSTRACT

A stent crimping tool for firmly and uniformly crimping a stent onto a balloon catheter is constructed from a crimping section holding the stent and the balloon catheter therein, wherein the crimping is actuated by a shaft having an input end and an output end, engaging the crimping section at the output end. The shaft has a detent formed into the input end. A gripping member has an internal cavity to receive the input end, and includes a hole proximate to the shaft, wherein a ball bearing and a compression spring are located within the hole to bias the ball bearing toward the shaft and to engage the detent. When a torque is applied to the gripping member, it is transmitted through the ball bearing to the shaft; if the torque exceeds a predetermined magnitude, it overcomes the force of the spring on the ball bearing causing the bearing to slide out of the detent thereby disconnecting the applied torque from the shaft. The crimping section can be a rubber tube having a lumen holding the stent and catheter. When the shaft compresses the rubber tube as it advances, the lumen collapses and crimps the stent onto the catheter. In another embodiment, the crimping section is a coiled filament suspended at both ends and having an axial space holding the stent and catheter. Rotating the shaft twists the filament which in turn constricts and crimps the stent onto the catheter.

5 Claims, 3 Drawing Sheets

U.S. PATENT DOCUMENTS

| | | |
|---|---|---|
| 4,373,923 | 2/1983 | Kilwin . |
| 4,468,224 | 8/1984 | Enzmann et al. . |
| 4,557,029 | 12/1985 | Stewart . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,786,271 | 11/1988 | Menn . |
| 4,838,264 | 6/1989 | Bremer et al. . |
| 4,864,924 | 9/1989 | Storace . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,263,969 | 11/1993 | Phillips . |
| 5,362,197 | 11/1994 | Hammersmark et al. . |
| 5,437,083 | 8/1995 | Williams et al. . |
| 5,437,524 | 8/1995 | Huang . |
| 5,465,716 | 11/1995 | Avitall . |
| 5,546,646 | 8/1996 | Williams et al. . |
| 5,626,474 | 5/1997 | Kukla et al. . |
| 5,626,604 | 5/1997 | Cottone, Jr. . |
| 5,630,830 | 5/1997 | Verbeek et al. . |
| 5,653,691 | 8/1997 | Rupp et al. . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |
| 5,836,952 | 11/1998 | Davis et al. . |
| 5,893,852 | 4/1999 | Morales . |
| 5,920,975 | 7/1999 | Morales . |
| 5,974,652 | 11/1999 | Kimes et al. . |
| 6,009,614 | 1/2000 | Morales . |

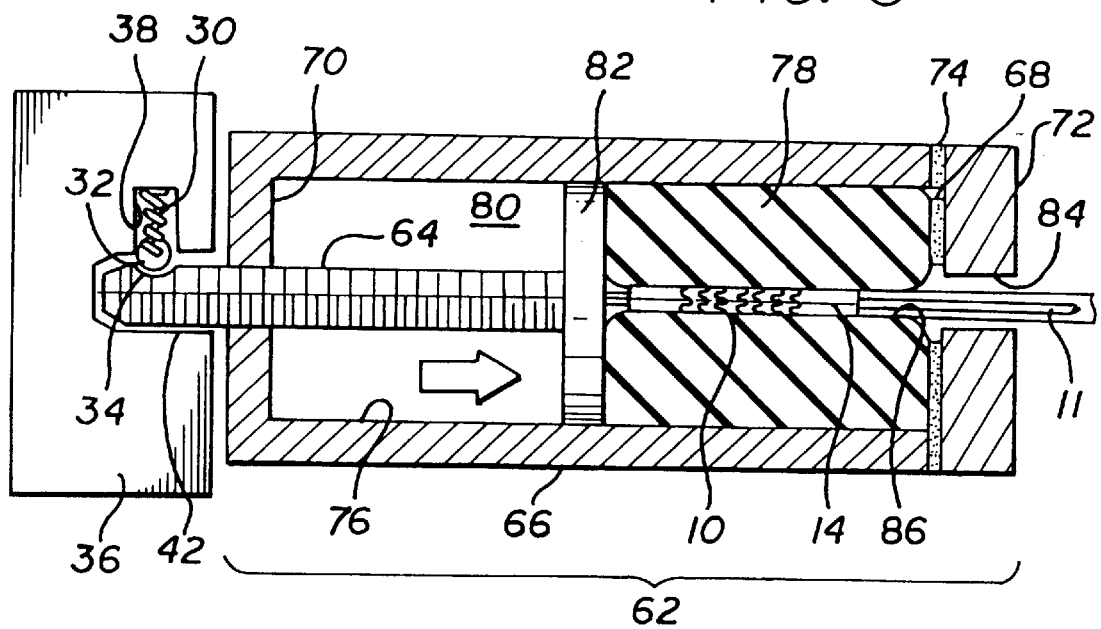
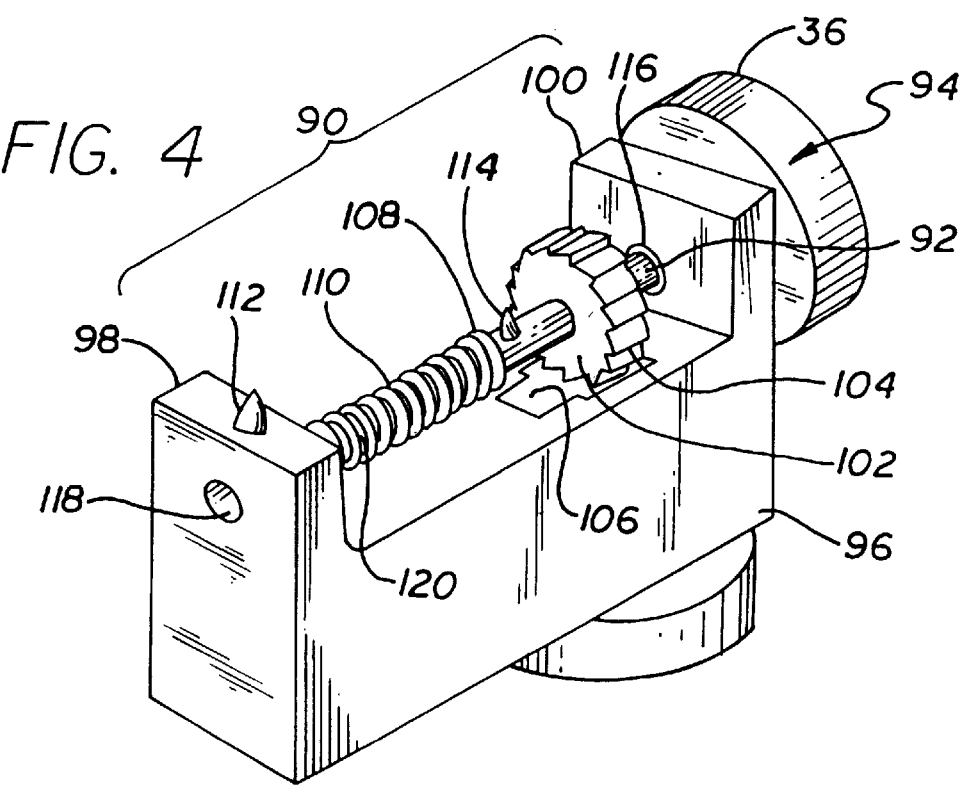

METHOD AND APPARATUS FOR UNIFORMLY CRIMPING A STENT ONTO A CATHETER

This application is a continuation of U.S. Ser. No. 09/072,925, now U.S. Pat. No. 5,974,692, filed May 5, 1998.

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which is antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps. Consequently, they are unsuitable for use by physicians in a cath lab who desire to crimp the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel. The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

The present invention is directed to a method and apparatus to obtain consistent crimping of a stent on a balloon catheter independent of the balloon profile. This is accomplished by limiting the amount of force that is applied to crimp the stent by using a clutch that disconnects the applied torque at a predetermined level.

In particular, the present invention is directed to a tool for crimping a stent onto a balloon catheter, comprising a crimping section holding the stent and the balloon catheter therein; a shaft having an input end and an output end, engaging the crimping section at the output end, which shaft when rotated actuates the crimping section to crimp the stent; a detent formed into the input end of the shaft; a gripping member having an internal cavity to receive the input end of the shaft, wherein the cavity includes a hole proximate to the shaft; a stop member; a biasing member disposed in the hole and biasing the stop member into engagement with the detent; whereby applying a torque to the gripping member beyond a predetermined level overcomes the force of the biasing member and slides the stop member out of the detent to disengage the applied torque from the shaft.

Rotation of the shaft halts, and the magnitude of the crimping force encountered by the stent levels off or drops off due to resilience or backlash in the system. Damage to the stent from excessive crimping force is avoided.

In one exemplary embodiment, the crimping section comprises a housing having an internal chamber with an enclosed first end, and an open second end having threads, wherein the output end of the shaft is partially disposed within the internal chamber through the open second end of the housing, and wherein the input end of the shaft includes threads that engage the threads of the internal chamber; and an elastic tubing having a lumen, wherein the tubing is disposed within the internal chamber adjacent the enclosed first end, and the output end of the shaft is disposed adjacent the tubing. Accordingly, the stent and balloon catheter are positioned within the lumen and rotation of the shaft advances the shaft into the tubing, compressing the tubing, and crimping the stent.

In another exemplary embodiment, the crimping section comprises a rigid chassis having a hollow interior enclosed by a closed back end and leading to an open front end, wherein the back end includes a threaded opening; an end cap enclosing the open front end, the end cap including a central opening; an elastic tube disposed within the hollow interior adjacent to the front end and having a length less than a length of the hollow interior to define a chamber adjacent to the back end; a piston slidably disposed within the chamber; wherein the shaft passes through the closed back end of the chassis and the shaft includes threads engaging the threads of the back end, and the output end of the shaft engages the piston so that the shaft when rotated displaces the piston to compress the elastic tube; whereby the stent is loaded onto the catheter and is inserted through the central opening into the elastic tube, and the compressed elastic tube squeezes the stent radially onto the catheter.

In yet another exemplary embodiment, the crimping section comprises a base having at least first and second spaced apart supports, wherein the shaft is rotatably disposed on the second support with the output end of the shaft extending toward the first support; a coiled filament having an axial space and being attached to the first support and the output end of the shaft and extending between the first and second supports; whereby inserting the stent and catheter into the axial space of the coiled filament and rotating the shaft reduces the diameter of the axial space thereby crimping the stent onto the catheter.

In conclusion, it is clear that the present invention tool can be adapted to a variety of stent crimping sections that are operated by application of torque. The clutch of the present invention ensures that the amount of force applied during the crimping process is controlled. This is achieved by disconnecting the gripping member from the shaft at a predetermined level of torque. Doing so disrupts the transfer of torque to the crimping section of the tool, which in turn levels the amount of crimping force exerted on the stent.

With precise control of applied crimping forces, the present invention tool is capable of homogeneously crimping a stent onto a balloon catheter. Such a crimping tool is highly useful to cardiologists, for example. Such physicians are often concerned with proper deployment of the stent within the patient that it is desirable to have a consistently and reliably crimped stent. The present invention tool is further a time saver, because the stent crimping procedure can be performed fairly efficiently and quickly. These and other advantages of the present invention will become apparent from the following detailed description thereof when taken in conjunction with the accompanying exemplary drawings.

BRIEF DESCRIPTION OF THE DRAWINGS

FIG. 3 is a cross-sectional view of an alternative embodiment of the present invention tool shown in FIG. 2.

FIG. 4 is a perspective view of an exemplary embodiment tool wherein the crimping section includes a coiled filament used to crimp the stent.

DETAILED DESCRIPTION OF THE PREFERRED EMBODIMENTS

Figure 1:
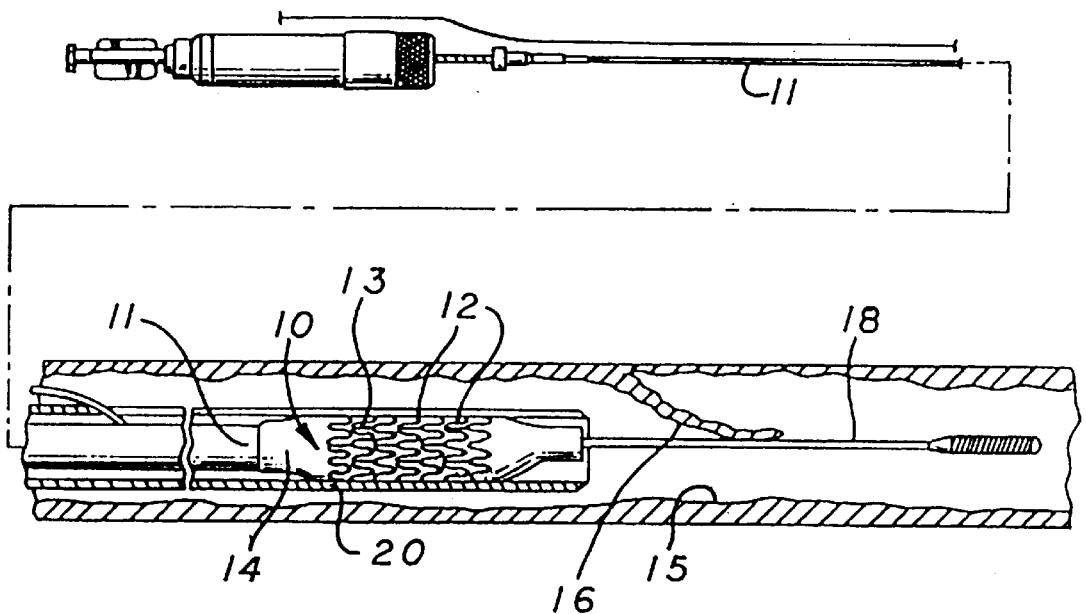
FIG. 1 is a side elevational view, partially in section, depicting a stent that has been crimped onto a delivery catheter and disposed within a vessel.

FIG. 1 illustrates intravascular stent 10 which is mounted onto delivery catheter 11. Stent 10 generally comprises a plurality of radially expandable cylindrical elements 12 disposed coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyvinyl chloride, polyethylene terephthalate and other like polymers. In order for stent 10 to remain in place on balloon 14 during delivery to the site of the damage within artery 15, stent 10 is compressed onto balloon 14.

An optional retractable protective delivery sleeve 20 may be provided to further ensure that stent 10 stays in place on balloon 14 of delivery catheter 1 1 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14.

In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the catheter-stent assembly is advanced over guide wire 18 within artery 15 until stent 10 is directly under detached lining 16. Prior to inflation of balloon 14, optional delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

Figure 2:
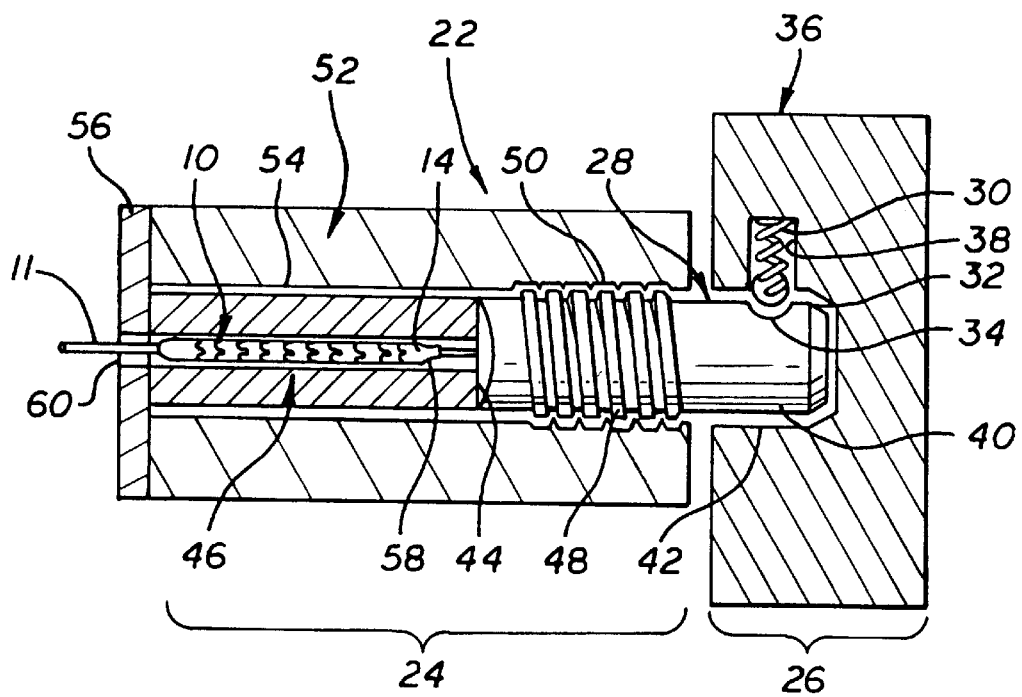
FIG. 2 is a sectional view of a preferred embodiment of the present invention, showing the clutch mechanism and the crimping section of the tool.

FIG. 2 is a cross-sectional view of a preferred embodiment of the present invention stent crimping tool 22. Stent crimping tool 22 as shown preferably has crimping section 24 and actuation section 26. Actuation section 26 is rotated and torque is transmitted through shaft 28 to crimping section 24.

In order to limit the amount of torque transmitted to shaft 28 and to thus limit the amount of crimping force, the present invention includes a clutch mechanism. In the preferred embodiment, the clutch mechanism includes compression spring 30, ball bearing 32, and detent 34 located on shaft 28. As gripping member 36, which can be a knob, crank, knurled spindle, or the like, is rotated, torque is transmitted through a stop member, here ball bearing 32, to detent 34. Spring 30 which is positioned within hole 38 biases ball bearing 32 into detent 34 with sufficient force to maintain the transfer of torque from gripping member 36 to shaft 28. If, however, a predetermined amount of torque is exceeded, the axial force of compression spring 30 is overcome causing ball bearing 32 to slide out of detent 34 and to retract into hole 38. Of course, this predetermined amount of torque can be adjusted by modifying the spring force, depth of the detent, size of the ball bearing, and other parameters known in the art.

At that instant, the linkage between gripping member 36 and shaft 28 is broken because ball bearing 32 is free to rotate and slide along the outer circumference of shaft 28. The clutch mechanism thus limits the torque delivery through shaft 28 into crimping section 24.

In the exemplary embodiment shown in FIG. 2, detent 34 is a semi-spherical cut-out formed in the input end 40 of shaft 28. Input end 40 is also received within cavity 42 of gripping member 36. Gripping member 36 may be formed in a cylindrical shape for easy gripping as shown, or may take other grippable shapes known in the art. Furthermore, a resilient piece of material may be used to replace spring 30 to bias ball bearing into shaft 28. For example, a sponge-like material can be used that has compliance and a level of resilience needed to urge ball bearing 32 into detent 34 in order to transfer torque between gripping member 36 and shaft 28.

At the opposite end of shaft 28 is output end 44 which is preferably located adjacent resilient tubing 46. Shaft 28 further includes external threads 48 meant to engage internal threads 50 formed inside housing 52 of crimping section 24. Resilient tubing 46 fits within hollow interior 54 of housing 52, wherein the latter is sufficiently rigid to not expand or distort under pressure. At the opposite end of housing 52 is end cap 56 that encloses the back end.

Thus, as the user manually rotates shaft 28 through application of torque to gripping member 36, shaft 28 advances into and compresses resilient tubing 46. Within resilient tubing 46 is lumen 58 containing uncrimped stent 10 already loaded onto balloon 14 of catheter 11. End cap 56 has an optional central opening 60 in communication with lumen 58. Hence, delivery catheter 11 can be inserted through central opening 60 and advanced into alignment with uncrimped stent 10 inside lumen 58. As compression of the resilient tubing 46 takes place, the length of resilient tubing 46 is shortened thereby causing lumen 58 to collapse and simultaneously crimp stent 10 onto delivery catheter 11. After the crimping step, shaft 28 is rotated in the opposite direction to retract it away from resilient tubing 46, which regains its original shape. Thereafter, the crimped stent and catheter assembly can be withdrawn through central opening 60.

In an alternative embodiment, a through hole (not shown) can be formed through the length of shaft 28 and through gripping member 36. After the crimping step, the crimped stent and catheter assembly can be advanced over a guide wire (not shown), passing through the through hole, and out the opposite end of the tool. Therefore, in this alternative embodiment, the crimped stent and catheter assembly can be immediately advanced over the guide wire to the patient for implantation after the crimping step.

During the crimping step, if maximum torque is exceeded, as explained above, ball bearing 32 slides out of detent 34. On the other hand, if gripping member 36 is continuously rotated, ball bearing 32 can be reseated within detent 34 during a subsequent revolution of gripping member 36 about input end 40, thereby re-engaging the linkage between shaft 28 and gripping member 36. At that moment, torque can be reapplied by rotating the gripping member 36 in either direction to advance or retract shaft 28. By alternately advancing and retracting shaft 28, it is possible to repeat the crimping step and ensure a firm and consistent crimp of stent 10 on catheter 11. To be sure, it is also possible to rotate delivery catheter 11 during each cycle of the crimping step.

FIG. 3 is an alternative embodiment of the exemplary embodiment shown in FIG. 2. More precisely, FIG. 3 is a cross-sectional view showing crimping section 62 that is a modification of crimping section 24 from FIG. 2. As seen in FIG. 3, torque is transferred between gripping member 36 and crimping section 62 through threaded shaft 64. Crimping section 62 is similar to that disclosed in co-pending U.S. patent application entitled "Indeflator-Driven, Rubber-Compression Crimping Tool" by Stephen A. Morales, (ACS-42071) Ser. No. 09/063,905, filed Apr. 21, 1998, whose entire contents are incorporated herein by reference.

In this embodiment, crimping section 62 is constructed from cylindrical shape chassis 66 having open end 68 and closed end 70. Open end 68 is sealed closed with optional end cap 72 that is bonded to open end 68 using adhesive 74 of a type known in the art. Optionally, end cap 72 may be attached to chassis 66 using threads, snaps, clamps, or other mechanical means known in the art.

Within cylindrical shape chassis 66 is hollow interior 76 that contains elastic tube 78 that is coaxially disposed within chassis 66. Notably, elastic tube 78 has a length that is shorter than the length of hollow interior 76. Because of this difference in length, and because elastic tube 78 is disposed adjacent open end 68, chamber 80 is formed adjacent to closed end 70. Slidably disposed within chamber 80 is movable piston 82. Shaft 64 engages piston 82 as shown in FIG. 3.

End cap 72 includes central opening 84 that is aligned and in communication with axial space 86 of elastic tube 78. Central opening 84 allows the stent-catheter assembly to be inserted into crimping section 62 prior to undergoing the crimping procedure.

Leading up to the procedure, a user introduces stent 10 already loaded onto balloon portion 14 of catheter 11 into axial space 86 within elastic tube 78. In the exemplary embodiment, the inside diameter of elastic tube 78 is slightly greater than the outside diameter of the uncrimped stent 10, or uncrimped stent and balloon 10 and 14, respectively.

As gripping member 36 is rotated, torque is transmitted through spring 30 to ball bearing 32 and to the walls of detent 34 formed in shaft 64. Shaft 64 once in rotation advances piston 82 into elastic tube 78 as indicated by the arrow. As a result, elastic tube 78 is compressed axially or lengthwise. The elastic material of elastic tube 78 must maintain a constant volume due to its surface elasticity and containment within the confines of hollow interior 76. Continuous compression of elastic tube 78 by piston 82 causes the material of elastic tube 78 to displace axially and then radially into axial space 86, in effect collapsing that space. This decreases the diameter of axial space 86. In turn, stent 10 contained inside axial space 86 is compressed radially onto balloon portion 14 of catheter 11.

As in the previously described embodiment, exceeding a pre-determined torque on gripping member 36 disengages ball bearing 32 from detent 34 to disconnect the application of torque to shaft 64. On the other hand, insofar as gripping member 36 and shaft 64 are linked through the clutch mechanism, it is possible to rotate and counter-rotate shaft 64 to advance and retract, respectively, piston 82. Indeed, it is possible to cycle through the crimping step over and over as necessary.

In the various exemplary embodiments of the present invention crimping tool shown in FIGS. 2 and 3, the housing pieces, piston, shafts, gripping member, etc. can be made from a rigid, injection molded plastic material. Also, translucent and transparent materials can be used so that the task at hand can be visually monitored. The present invention design is well suited for fabrication from surgical steel, too. Resilient tubing 46 and elastic tube 78 of each embodiment can be made from rubber or other elastomers known in the art.

FIG. 4 is a perspective view of an alternative embodiment of the present invention tool. In this embodiment, stent crimping section 90 contains a filament used to constrict a stent onto a balloon catheter inserted within an axial space formed by the coiled filament. Torque is still applied through gripping member 36, which is connected to shaft 92. As best seen in this figure, the surface of gripping member 36 may optionally be contoured or knurled by pattern 94 to provide a better gripping surface.

Stent crimping section 90 is similar to that disclosed in co-pending U.S. patent application entitled "Stent Crimping Tool and Method of Use" by Stephen A. Morales, (ACS-42070) Ser. No. 08/962,632, filed Nov. 3, 1997, the entire contents of which are incorporated herein by reference. In FIG. 4, stent crimping section 90 includes base 96, first vertical support 98, second vertical support 100, wherein the two vertical supports 98 and 100 are spaced apart on base 96. Shaft 92 rotatably passes through an opening in second vertical support 100. Cam 102 is affixed on shaft 92 whereby the cam rotates with shaft 92.

Cam 102 optionally includes an obstruction which, in the preferred embodiment, are teeth 104 located at the circumference of cam 102 and are designed to engage pawl 106. Pawl 106 is positioned on base 96 and biased into teeth 104. Together, cam 102, teeth 104, and pawl 106 form a ratchet mechanism that permits rotation in one direction yet prevents rotation of shaft 92 in the opposite direction.

Attached to output end 108 of shaft 92 is one end of coiled filament 110. The opposite end of coiled filament 110 is connected to first vertical support 98. In the preferred embodiment shown in FIG. 4, coiled filament 110 is a coiled tension spring with its ends hooked to pins 112 and 114.

In FIG. 4, the present invention tool has fairly high extending vertical supports 98, 100, such that shaft 92 passes through second vertical support 100 rather than just resting upon it. Optional bearing 116 is located inside second vertical support 100 to minimize rotational friction between shaft 92 and second vertical support 100.

Also, through hole 118 is provided in first vertical support 98 and is in communication with axial space 120 that is defined by the collection of coils of coiled filament 110. When the tool is used, through hole 118 allows the stent-catheter assembly to be passed therethrough into axial space 120.

Figure 5:
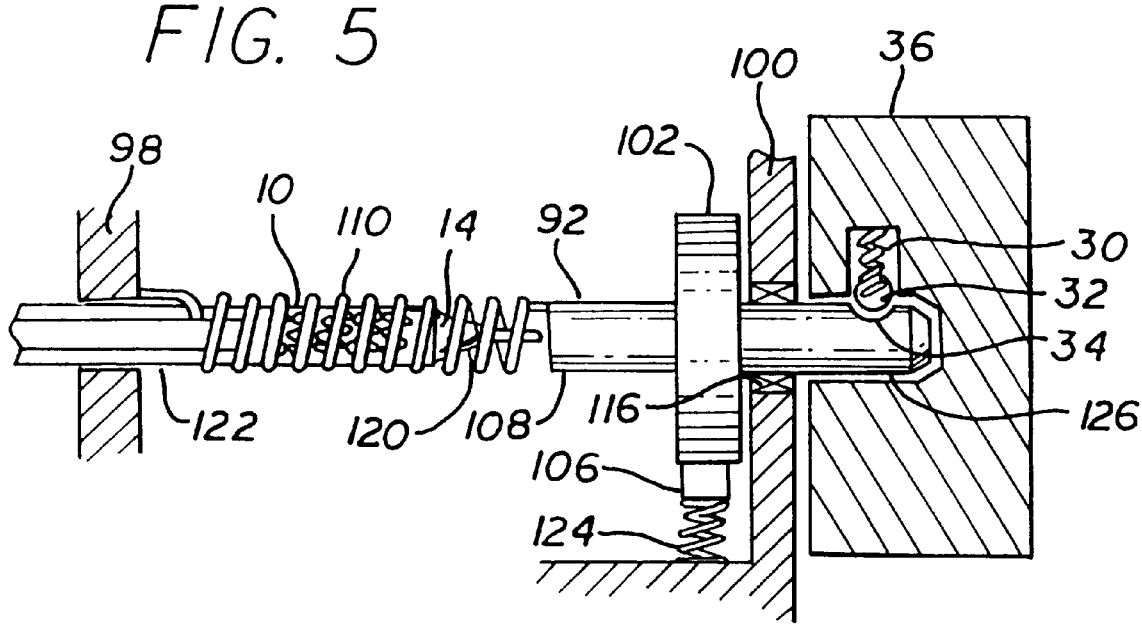
FIGS. 5 and 6 are simplified schematic diagrams depicting a stent crimping operation performed by the present invention tool.
Figure 6:
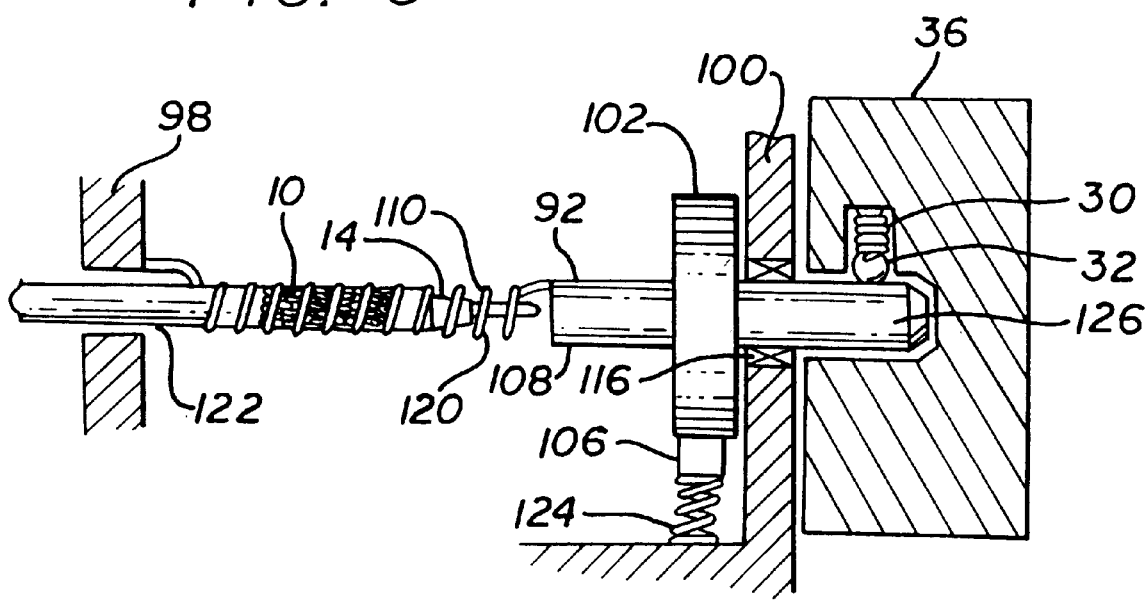

FIGS. 5 and 6 are simplified schematic diagrams of the preferred embodiment of the present invention shown in FIG. 4 to help explain the crimping operation. Specifically, FIG. 5 provides a side elevational view of the present invention whereby stent 10 and balloon 14 have been inserted within axial space 120. Optional sheath 122 is shown covering the stent-catheter assembly. Inside gripping member 36, ball bearing 32 has been biased by compression spring 30 into detent 34. Gripping member 36 can be rotated to apply torque through shaft 92 thereby twisting coiled filament 110 in order to constrict the stent-catheter assembly inside axial space 120.

FIG. 6 shows completion of the crimping step after coiled filament 110 has been twisted. Also shown in FIG. 6 is the instant when maximum torque has been exceeded so that ball bearing 32 has slid out of detent 34 and is riding on the outside diameter of shaft 92. At this very instant, the applied torque from gripping member 36 is disconnected from shaft 92 and from constricted coiled filament 110. The natural resiliency of coiled filament 110 at this moment tends to counter-rotate shaft 92. However, pawl 106 biased by spring 124 engages cam 102 to prevent the counter-rotation. Of course, disengagement of pawl 106 from cam 102 would permit free rotation of shaft 92 in either direction. At input end 126 of shaft 92, shaft 92 rotates independently of gripping member 36 until ball bearing 32 is again seated within detent 34 during one of the revolutions of shaft 92 relative to gripping member 36. Upon re-engagement, gripping member 36 is again linked to shaft 92 to control its rotation.

In the preferred embodiment, parts forming crimping section 90 are made from Nylon or a comparable polymer known in the art. Coiled filament 110 can be a metal tension spring, a resilient polymer ribbon made from Mylar, for example, formed into a coil. The coiled filament can have a flat, polygonal, or round cross-sectional shape.

The present invention is preferably sterilized and intended to be used in a cath lab by a trained technician or cardiologist. As will be appreciated by those skilled in the art, the present invention crimping tool is designed both for single use applications in a cath lab by a physician, or for multiple use applications in a sterile environment in a high volume manufacturing facility. In such a manufacturing facility where sterile conditions exist, the present invention stent crimping tool can be used repeatedly to crimp stents onto balloons until the mechanism wears out. Thus, repeated uses of the present invention are contemplated for controlled, sterile environments, as are single use applications when operated by cath lab personnel.

Furthermore, the present invention crimping tool can be used with any stent that is released without a delivery system. The crimping tool may also be sold alone, because its design is robust enough to undergo many uses.

Other modifications can be made to the present invention without departing from the scope thereof. The specific dimensions, procedural steps, and materials of construction are provided as examples, and substitutes are readily contemplated which do not depart from the invention.

What is claimed is:

1. A stent crimping tool, comprising:

a crimping section holding the stent and the balloon catheter therein;

a shaft having an input end and an output end, engaging the crimping section at the output end, which shaft when rotated actuates the crimping section to crimp the stent;

a detent formed into the input end of the shaft;

a gripping member having an internal cavity to receive the input end of the shaft, wherein the cavity includes a hole proximate to the shaft;

a stop member;

a biasing member disposed in the hole and biasing the stop member into engagement with the detent;

a base having at least first and second spaced apart supports;

wherein the shaft is rotatably disposed on the second support with the output end of the shaft extending toward the first support;

a coiled filament having an axial space and being attached to the first support and the output end of the shaft and extending between the first and second supports;

whereby inserting the stent and catheter into the axial space of the coiled filament and rotating the shaft reduces the diameter of the axial space thereby crimping the stent onto the catheter.

2. The stent crimping tool according to claim 1, wherein the coiled filament includes a coiled spring.

3. The stent crimping tool according to claim 1, wherein the coiled filament includes a flat cross-sectional shape.

4. The stent crimping tool according to claim 1, wherein the crimping tool further comprises:

a cam affixed to the shaft and having an obstruction at a circumference thereof; and a pawl disposed on the base and biased in to engagement with the cam obstruction to prevent free rotation of the shaft.

5. The stent crimping tool according to claim 1, wherein the tool further includes a sheath at least partially covering the stent and catheter.

* * * * *

UNITED STATES PATENT AND TRADEMARK OFFICE
CERTIFICATE OF CORRECTION

PATENT NO. : 6,108,886
DATED : Aug. 29, 2000
INVENTOR(S) : Richard M. Kimes, Michael S. Mirizzi It is certified that error appears in the above-identified patent and that said Letters Patent is hereby corrected as shown below:

Title page, in the title, delete "METHOD AND".

Column 1, line 1, delete "METHOD AND".

Signed and Sealed this

Twenty-fourth Day of April, 2001

Attest:

NICHOLAS P. GODICI

*Attesting Officer*     *Acting Director of the United States Patent and Trademark Office*